United States Patent
Ahonen et al.

(10) Patent No.: US 10,463,731 B2
(45) Date of Patent: Nov. 5, 2019

(54) ADJUVANT COMBINATIONS COMPRISING ALPHA-GALACTOSYLCERAMIDE OR IGB3, CD40 AGONISTS AND ANTIGEN

(71) Applicant: IMMURX, INC., Lebanon, NH (US)

(72) Inventors: Cory Ahonen, Enfield, NH (US); Randolph Noelle, Plainfield, NH (US)

(73) Assignee: IMMURX, INC., Lebanon, NH (US)

( * ) Notice: Subject to any disclaimer, the term of this patent is extended or adjusted under 35 U.S.C. 154(b) by 443 days.

(21) Appl. No.: 14/963,946

(22) Filed: Dec. 9, 2015

(65) Prior Publication Data

US 2016/0158348 A1 Jun. 9, 2016

Related U.S. Application Data

(62) Division of application No. 14/324,700, filed on Jul. 7, 2014, now Pat. No. 9,238,067, which is a division of application No. 12/597,615, filed as application No. PCT/US2008/005341 on Apr. 25, 2008, now Pat. No. 8,802,098.

(60) Provisional application No. 60/907,976, filed on Apr. 25, 2007.

(51) Int. Cl.
| | | |
|---|---|---|
| A61K 39/39 | (2006.01) | |
| A61K 39/29 | (2006.01) | |
| A61K 39/00 | (2006.01) | |
| A61K 39/395 | (2006.01) | |
| A61K 45/06 | (2006.01) | |
| C07K 16/28 | (2006.01) | |
| A61K 31/7032 | (2006.01) | |
| C07K 16/46 | (2006.01) | |

(52) U.S. Cl.
CPC .......... *A61K 39/39* (2013.01); *A61K 31/7032* (2013.01); *A61K 39/29* (2013.01); *A61K 39/3955* (2013.01); *A61K 39/39541* (2013.01); *A61K 45/06* (2013.01); *C07K 16/2878* (2013.01); *C07K 16/468* (2013.01); *A61K 2039/505* (2013.01); *A61K 2039/55511* (2013.01); *A61K 2039/55516* (2013.01); *A61K 2039/57* (2013.01); *C07K 2317/21* (2013.01); *C07K 2317/24* (2013.01); *C07K 2317/31* (2013.01); *C07K 2317/74* (2013.01); *C07K 2317/75* (2013.01); *C07K 2317/76* (2013.01)

(58) Field of Classification Search
None
See application file for complete search history.

(56) References Cited

U.S. PATENT DOCUMENTS

| 6,410,711 B1 | 6/2002 | Armitage et al. |
| 8,802,098 B2 | 8/2014 | Ahonen et al. |
| 2004/0141950 A1 | 7/2004 | Noelle et al. |
| 2004/0258688 A1 | 12/2004 | Hawiger et al. |
| 2006/0078994 A1 | 4/2006 | Healey et al. |
| 2006/0093612 A1 | 5/2006 | Srivastava |
| 2006/0195067 A1 | 8/2006 | Wolter et al. |
| 2006/0211856 A1 | 9/2006 | Tsuji et al. |
| 2006/0222654 A1 | 10/2006 | Delcayre et al. |
| 2006/0292119 A1 | 12/2006 | Chen et al. |
| 2007/0148163 A1 | 6/2007 | Takahashi et al. |

FOREIGN PATENT DOCUMENTS

| WO | 2003063899 | 8/2003 |
| WO | 2006026389 | 3/2006 |
| WO | 2006029010 | 3/2006 |
| WO | 2006042177 | 4/2006 |
| WO | 2007007946 | 1/2007 |
| WO | 2007070623 | 6/2007 |

OTHER PUBLICATIONS

Rudikoff et al., Proc Natl Acad Sci USA 79: 1979-1983 (1982). (Year: 1982).*
Colman, Research in Immunology 145: 33-36 (1994). (Year: 1994).*
Kussie et al., J. Immunol. 152: 146-152 (1994). (Year: 1994).*
Vonderheide et al., Clin Cancer Res 19: 1035-1043 (2013). (Year: 2013).*
Chen et al., EMBO J., 14: 2784-2794 (1995). (Year: 1995).*
Barr et al. "CD40 antibody as a potent immunological adjuvant: CD40 antibody provides the CD40 signal to B cells, but does not substitute for T cell help in responses to TD antigens" Vaccine, vol. 23, No. 26, (2005), pp. 3477-3482.
Hermans et al., "NKT cells enhance CD4+ and CD8+ T cell responses to soluble antigen in vivo through direct interaction with dendritic cells," J Immunol. Nov. 15, 2003;171(10):5140-7.
International Search Report, dated Jul. 22, 2008, PCT Application No. PCT/US08/005341.
Uldrich et al. "NKT cell stimulation with glycolipid antigen in vivo: Costimulation-dependent expansion, Bim-dependent contraction, and hyporesponsiveness to further antigenic challenge" Journal of immunology. vol. 175. No. 5 (2005), pp. 3092-3101.

* cited by examiner

*Primary Examiner* — Phillip Gambel
(74) *Attorney, Agent, or Firm* — Robin L. Teskin; Baker, Donelson, Bearman, Caldwell & Berkowitz PC (57) ABSTRACT

Adjuvant combinations comprising at least one NKT activator, such as alpha-galactosylceramide (α-Gal-Cer) or iGb3, a CD40 agonist and optionally an antigen are disclosed. The use of these immune adjuvants for treatment of various chronic diseases such as cancers is also provided.

13 Claims, 5 Drawing Sheets

Specification includes a Sequence Listing.

Figure 1. Combined administration of anti-CD40 and α-GalCer synergistically enhances the expansion of antigen-specific T cells *in vivo*.

Figure 2. Quantifying immune responses as a result of immunization with combined anti-CD40 and α-GalCer.

Figure 3. CD40/TLR* vaccination therapeutically intervenes in systemic melanoma.

Figure 4. anti-CD40 and α-GalCer induces CD70 expression on DCs *in vivo*.

Figure 5: α-GalCer/CD40 immunization elicits a potent CD8+ T cell response that is STAT4, IFNg, IFNab independent but is STAT1 and T-bet dependent.

SEQUENCE LISTING

```
<160> NUMBER OF SEQ ID NOS: 1

<210> SEQ ID NO 1
<211> LENGTH: 9
<212> TYPE: PRT
<213> ORGANISM: Artificial Sequence
<220> FEATURE:
<223> OTHER INFORMATION: peptide

<400> SEQUENCE: 1

Ser Val Tyr Asp Phe Phe Val Trp Leu
1               5
```

ADJUVANT COMBINATIONS COMPRISING ALPHA-GALACTOSYLCERAMIDE OR IGB3, CD40 AGONISTS AND ANTIGEN

CROSS-REFERENCE TO RELATED APPLICATIONS

This application is a divisional of U.S. application Ser. No. 14/324,700, filed Jul. 7, 2014, which is a divisional of U.S. application Ser. No. 12/597,615, filed May 13, 2010, now U.S. Pat. No. 8,802,098, which is a U.S. National Stage of International Application No. PCT/US2008/005341, international filing date Apr. 25, 2008, which claims the benefit of U.S. Provisional Application No. 60/907,976, filed Apr. 25, 2007, the disclosure of each of which is herein incorporated by reference in its entirety.

FIELD OF THE INVENTION

The invention generally relates to synergistic adjuvant combinations which upregulate CD70 expression on immune cells and promote antigen specific cellular immunity. More particularly, the invention relates to a specific synergistic combination comprising a Natural Killer T cell (NKT) activator, e.g., alpha-galactosylceramide (α-Gal-Cer) or iGb3, and a CD40 agonist, e.g., an agonistic anti-CD40 antibody or a CD40L polypeptide or conjugate, and optionally further including a target antigen. Still further the invention provides novel immune therapies comprising the administration of such synergistic adjuvant combinations or protein conjugates to enhance antigen specific cellular immunity, i.e., CD8+ immunity. Specifically, the use of compositions comprising these adjuvant combinations and/or or polypeptide conjugates as immune adjuvants for treating various chronic diseases including cancer, infectious diseases, autoimmune diseases, allergic and inflammatory diseases is also taught.

This application includes as part of its disclosure a biological sequence listing which is being concurrently submitted through EFS-Web. Said biological sequence listing is contained in a file named "4325904604.txt" which was created Dec. 18, 2018, and has a size of 695 bytes, and is hereby incorporated by reference in its entirety.

BACKGROUND OF THE INVENTION

The body's defense system against microbes as well as the body's defense against other chronic diseases such as those affecting cell proliferation is mediated by early reactions of the innate immune system and by later responses of the adaptive immune system. Innate immunity involves mechanisms that recognize structures which are for example characteristic of the microbial pathogens and that are not present on mammalian cells. Examples of such structures include bacterial liposaccharides (LPS), viral double stranded DNA, and unmethylated CpG DNA nucleotides. The effector cells of the innate immune response system comprise neutrophils, macrophages, and natural killer cells (NK cells). In addition to innate immunity, vertebrates, including mammals, have evolved immunological defense systems that are stimulated by exposure to infectious agents and that increase in magnitude and effectiveness with each successive exposure to a particular antigen. Due to its capacity to adapt to a specific infection or antigenic insult, this immune defense mechanism has been described as adaptive immunity. There are two types of adaptive immune responses, called humoral immunity, involving antibodies produced by B lymphocytes, and cell-mediated immunity, mediated by T lymphocytes.

Two types of major 'T' lymphocytes have been described, CD8+ cytotoxic lymphocytes (CTLs) and CD4 helper cells (Th cells). CD8+ T cells are effector cells that, via the T cell receptor (TCR), recognize foreign antigens presented by class I MHC molecules on, for instance, virally or bacterially infected cells. Upon recognition of foreign antigens, CD8+ cells undergo an activation, maturation and proliferation process. This differentiation process results in CTL clones which have the capacity of destroying the target cells displaying foreign antigens. T helper cells on the other hand are involved in both humoral and cell-mediated forms of effector immune responses. With respect to the humoral, or antibody immune response, antibodies are produced by B lymphocytes through interactions with Th cells. Specifically, extracellular antigens, such as circulating microbes, are taken up by specialized antigen-presenting cells (APCs), processed, and presented in association with class II major histocompatibility complex (MHC) molecules to CD4+ Th cells. These Th cells in turn activate B lymphocytes, resulting in antibody production. The cell-mediated, or cellular, immune response, in contrast, functions to neutralize microbes which inhabit intracellular locations, such as after successful infection of a target cell. Foreign antigens, such as for example, microbial antigens, are synthesized within infected cells and resented on the surfaces of such cells in association with Class I MHC molecules. Presentation of such epitopes leads to the above-described stimulation of CD8+ CTLs, a process which in turn is also stimulated by CD4+ Th cells. Th cells are composed of at least two distinct subpopulations, termed Th1 and Th2 cells. The Th1 and Th2 subtypes represent polarized populations of Th cells which differentiate from common precursors after exposure to antigen.

Each T helper cell subtype secretes cytokines that promote distinct immunological effects that are opposed to one another and that cross-regulate each other's expansion and function. Th1 cells secrete high amounts of cytokines such as interferon (MN) gamma, tumor necrosis factor-alpha (TNF-alpha), interleukin-2 (IL-2), and IL-12, and low amounts of IL-4. Th1 associated cytokines promote CD8+ cytotoxic T lymphocyte T lymphocyte (CTL) activity and are most frequently associated with cell-mediated immune responses against intracellular pathogens. In contrast, Th2 cells secrete high amounts of cytokines such as IL-4, IL-13, and IL-10, but low IFN-gamma, and promote antibody responses. Th2 responses are particularly relevant for humoral responses, such as protection from anthrax and for the elimination of helminthic infections.

Whether a resulting immune response is Th1 or Th2-driven largely depends on the pathogen involved and on factors in the cellular environment, such as cytokines. Failure to activate a T helper response, or the correct T helper subset, can result not only in the inability to mount a sufficient response to combat a particular pathogen, but also in the generation of poor immunity against reinfection. Many infectious agents are intracellular pathogens in which cell-mediated responses, as exemplified by Th1 immunity, would be expected to play an important role in protection and/or therapy. Moreover, for many of these infections it has been shown that the induction of inappropriate Th2 responses negatively affects disease outcome. Examples include *M. tuberculosis, S. mansoni*, and also counterproductive Th2-like dominated immune responses. Lepromatous leprosy also appears to feature a prevalent, but inappropriate, Th2-like response. HIV infection represents another example. There, it has been suggested that a drop in the ratio of Th1-like cells to other Th cell populations can play a critical role in the progression toward disease symptoms.

As a protective measure against infectious agents, vaccination protocols for protection from some microbes have been developed. Vaccination protocols against infectious pathogens are often hampered by poor vaccine immunogenicity, an inappropriate type of response (antibody versus cell-mediated immunity), a lack of ability to elicit long-term immunological memory, and/or failure to generate immunity against different scrotypes of a given pathogen. Current vaccination strategies target the elicitation of antibodies specific for a given serotype and for many common pathogens, for example, viral serotypes or pathogens. Efforts must be made on a recurring basis to monitor which serotypes are prevalent around the world. An example of this is the annual monitoring of emerging influenza A serotypes that are anticipated to be the major infectious strains.

To support vaccination protocols, adjuvants that would support the generation of immune responses against specific infectious diseases further have been developed. For example, aluminum salts have been used as a relatively safe and effective vaccine adjuvants to enhance antibody responses to certain pathogens. One of the disadvantages of such adjuvants is that they are relatively ineffective at stimulating a cell-mediated immune response and produce an immune response that is largely Th2 biased.

It is now widely recognized that the generation of protective immunity depends not only on exposure to antigen, but also the context in which the antigen is encountered. Numerous examples exist in which introduction of a novel antigen into a host in a non-inflammatory context generates immunological tolerance rather than long-term immunity whereas exposure to antigen in the presence of an inflammatory agent (adjuvant) induces immunity. (Mondino et al., Proc. Natl. Acad. Sci., USA 93:2245 (1996); Pulendran et al., J. Exp. Med. 188:2075 (1998); Jenkins et al., Immunity 1:443 (1994); and Kearney et al., Immunity 1:327 (1994)).

A naturally occurring molecule known to regulate adaptive immunity is CD40. CD40 is a member of the TNF receptor superfamily and is essential for a spectrum of cell-mediated immune responses and required for the development of T cell dependent humoral immunity (Aruffo et al., Cell 72:291 (1993); Farrington et al., Proc Natl Acad Sci., USA 91:1099 (1994); Renshaw et al., J Exp Med 180:1889 (1994)). In its natural role, CD40-ligand expressed on CD4+ T cells interacts with CD40 expressed on DCs or B cells, promoting increased activation of the APC and, concomitantly, further activation of the T cell (Liu et al Semin Immunol 9:235 (1994); Bishop et al., Cytokine Growth Factor Rev 14:297 (2003)). For DCs, CD40 ligation classically leads to a response similar to stimulation through TLRs such as activation marker upregulation and inflammatory cytokine production (Quezada et al. Annu Rev Immunol 22:307 (2004); O'Sullivan B and Thomas R Crit Rev Immunol 22:83 (2003)). Its importance in CD8 responses was demonstrated by studies showing that stimulation of APCs through CD40 rescued CD4-dependent CD8+ T cell responses in the absence of CD4 cells (Lefrancois et al., J Immunol. 164:725 (2000); Bennett et al., Nature 393:478 (1998); Ridge et al., Nature 393:474 (1998); Schoenberger et al., Nature 393:474 (1998). This finding sparked much speculation that CD40 agonists alone could potentially rescue failing CD8+ T cell responses in some disease settings.

Other studies, however, have demonstrated that CD40 stimulation alone insufficiently promotes long-term immunity. In some model systems, anti-CD40 treatment alone insufficiently promoted long-term immunity. In some model systems, anti-CD40 treatment alone can result in ineffective inflammatory cytokine production, the deletion of antigen-specific T cells (Mauri et al. Nat Med 6:673 (2001); Kedl et al. Proc Natl Acad Sci., USA 98:10811 (2001)) and termination of B cell responses (Erickson et al., J Clin Invest 109:613 (2002)). Also, soluble trimerized CD40 ligand has been used n the clinic as an agonist for the CD40 pathway and what little has been reported is consistent with the conclusion that stimulation of CD40 alone fails to reconstitute all necessary signals for long term CD8+ T cell immunity (Vonderheide et al., J Clin Oncol 19:3280 (2001)).

Various agonistic antibodies have been reported by different groups. For example, one mAb CD40.4 (5c3) (PharMingen, San Diego Calif.) has been reported to increase the activation between CD40 and CD40L by approximately 30-40%. (Schlossman et al., Leukocyte Typing, 1995, 1:547-556). Also, Seattle Genetics in U.S. Pat. No. 6,843,989 allege to provide methods of treating cancer in humans using an agonistic anti-human CD40 antibody. Their antibody is purported to deliver a stimulatory signal, which enhances the interaction of CD40 and CD40L by at least 45% and enhances CD40L-mediated stimulation and possess in vivo neoplastic activity. They obtain this antibody from S2C6, an agonistic anti-human CD40 antibody previously shown to deliver strong growth-promoting signals to B lymphocytes. (Paulie et al., 1989, J. Immunol. 142:590-595).

Because of the activity of CD40 in innate and adaptive immune responses, various CD40 agonists have been explored for usage as vaccine adjuvants and in therapies in wherein enhanced cellular immunity is desired. Recently, it was demonstrated that immunization with antigen in combination with some TLR agonists and anti-CD40 treatment (combined TLR/CD40 agonist immunization) induces potent CD8+ T cell expansion, eliding a response 10-20 fold higher than immunization with either agonist alone (Ahonen et al., J Exp Med 199:775 (2004)). This was the first demonstration that potent CD8+ T cell responses can be generated in the absence of infection with a viral or microbial agent. Antigen specific CD8+ T cells elicited by combined TLR/CD40 agonist immunization demonstrate lytic function, gamma interferon production, and enhanced secondary responses to antigenic challenge. Synergistic activity with anti-CD40 in the induction of CD8+ T cell expansion has been shown with agonists of TLR1/6, 2/6, 3, 4, 5, 7 and 9. This suggests that combined TLR/CD40 agonist immunization can reconstitute all of the signals required to elicit profound acquired cell-mediated immunity.

It is known that NKT cells are immunoregulatory T-lymphocytes that express a T cell receptor which is restricted by the non-polymorphic CD1d antigen presenting molecule. NKT cells recognize the CD1d-presented glycolipid, alpha-galactosylceramide (α-Gal-Cer). Upon recognition of α-Gal-Cer, NKT cells become activated and produce cytokines including IL-4, IL-10, IL-13 and IFN-γ, and as such, they can either upregulate or downregulate immune responses by promoting the secretion of immune regulatory cytokines. Mice which are devoid of NKT cells are more susceptible to bacterial infections and resistance to some tumors, demonstrating an important role for NKT cells in host defense. It has also been shown that activation of NKT cells by the administration of α-Gal-Cer, as a monotherapy, to mice can enhance the immunity to tumors with limited success (Matsuyoshi, H., S. Hirata, Y. Yoshitake, Y. Motomura, D. Fukuma, A. Kurisaki, T. Nakatsura, Y. Nishimura, and S. Senju. 2005. Therapeutic effect of alpha-galactosylceramide-loaded dendritic cells genetically engineered to express SLC/CCL21 along with tumor antigen against peritoneally disseminated tumor cells. *Cancer Sci.* 96:889-896; Crowe, N.Y., J. M. Coquet, S. P. Berzins, K. Kyparissoudis, R. Keating, D. G. Pellicci, Y. Hayakawa, D. I. Godfrey, and M. J. Smyth. 2005. Differential antitumor immunity mediated by NKT cell subsets in vivo. *J. Exp. Med.* 202:1279-1288; Smyth, M. J., N. Y. Crowe, Y. Hayakawa, K. Takeda, H. Yagita, and D. I. Godfrey. 2002. NKT cells—conductors of tumor immunity? *Curr. Opin. Immunol.* 14:165-171).

To increase the effectiveness of an adaptive immune response, such as in a vaccination protocol or during a microbial infection, it is therefore important to develop novel, more effective, vaccine adjuvants. The present invention satisfies this need and provides other advantages as well. Previously, the present inventors have reported novel synergistic adjuvants comprising the combination of a toll like receptor (TLR) agonist and a CD40 agonist. These agonists in combination elicit a synergistic effect on cellular immunity. These synergistic adjuvants and the prophylactic and therapeutic applications thereof are disclosed in US published patent application US20040141950 published on Jul. 22, 2004, and which patent application is incorporated by reference in its entirety herein. This invention relates to the discovery of another synergistic adjuvant combination and the use thereof as a therapeutic or prophylactic immune potentiating combination.

SUMMARY OF THE INVENTION

This invention relates to synergistic immune adjuvants comprising the combination of (i) at least one NKT activator, e.g., alpha-galactosylceramide (α-GalCer) or iGb3; and (ii) at least one CD40 agonist such as a CD40 agonistic antibody or fragment thereof or a CD40L polypeptide such as a monomeric or multimeric (trimeric) CD40L protein, CD40L protein fragment, or conjugate containing CD40L and (iii) optionally an antigen against which a cellular immune response is desirably elicited. The present invention further relates to the use of such combinations as immune adjuvants and for treating conditions wherein T cell immunity is desirably enhanced.

As described in detail infra, these immune combinations may be administered to a host in need of such treatment as a means of:
  (i) inducing higher frequencies of antigen-specific CD8+ T cells relative to the administration of only a CD40 agonist or an NKT activator;
  (ii) inducing higher quantities of antigen-specific CD8+ T cells relative to the administration of only a CD40 agonist or an NKT activator; and
  (iii) enhancing tumor immunity relative to the administration of only a CD40 agonist or an NKT activator.

These immune adjuvant combinations which optionally may further include an antigen may be used in treating any disease or condition wherein the above-identified enhanced cellular immune responses are therapeutically desirable, especially infectious diseases, proliferative disorders such as cancer, allergy, autoimmune disorders, inflammatory disorders, and other chronic diseases wherein enhanced cellular immunity is a desired therapeutic outcome. Preferred applications of the invention include especially the treatment of a chronic disease such as cancer.

DETAILED DESCRIPTION OF THE INVENTION

The present invention relates to the use of a synergistic immune adjuvant combination comprising synergistically effective amounts of (i) at least one natural killer-T cell (NKT) activating agent such as alpha-galactosylceramide (α-GalCer) or another NKT cell activating agent; (ii) at least one CD40 agonist and (ii) optionally at least one antigen. These adjuvants may be used to (i) expand antigen-specific effector CD8 T cells, and/or (ii) to enhance immune responses. Based thereon these synergistic adjuvants can be used prophylactically and therapeutically to treat subjects having conditions wherein enhanced cellular immunity is desired such as cancer and other proliferative disorders, viral and other infections, autoimmunity, inflammatory diseases and allergic disorders. Particularly, the subject synergistic adjuvants may be used vaccine adjuvant. The basic components of such a vaccine adjuvant would therefore be an NKT cell activator, a CD40 agonist and the addition of a tumor or infectious disease antigen, if warranted. Such an invention would be useful in any situation where one would like to enhance immune responses, like cancer or infectious disease, or modify immune responses like in autoimmunity.

More specifically, the present invention provides a novel synergistic agonistic combination comprising an NKT activator, e.g., alpha-galactosylceramide (α-Gal-Cer) or iGb3 and a CD40 agonist (for example a CD40L protein or fragment or derivative or multimeric thereof or an agonistic antibody or antibody fragment that binds CD40, preferably human CD40) and optionally an antigen. These adjuvant combinations when administered to a host, preferably a human, may be used to generate enhanced antigen specific cellular immune responses.

In preferred embodiments the NKT activator is alpha-galactosylceramide (α-Gal-Cer), isoglobotrihexosylceramide (iGb3) or any other molecules which can stimulate NKT such as, for example, other glycolipids presented by CD1d antigen-presenting molecules.

Also, the invention provides methods of using said synergistic adjuvant combinations and vehicles containing to a host in which an antigen specific immune response is desirably elicited, for example a person with a chronic disease such as cancer or an infectious or allergic disorder producing said composition.

Still further the invention provides compositions comprising said novel synergistic NKT activator/CD40 agonist combinations which are suitable for administration to a host in order to elicit an enhanced antigen-specific cellular immune response.

Particularly, the invention provides novel methods of immunotherapy comprising the administration of said novel synergistic adjuvant combination to a host in need of such treatment in order to elicit an enhanced antigen specific cellular immune response. In preferred embodiments these compositions and conjugates will be administered to a subject with or at risk of developing a cancer, an infection, particularly a chronic infectious diseases e.g., involving a virus, bacteria or parasite; or an autoimmune, inflammatory or allergic condition. Particularly, in a preferred embodiment, the invention may be used to elicit antigen specific cellular immune responses against melanoma.

Thus, this invention provides for the development of potent vaccines against cancer and other proliferative diseases such as autoimmune diseases, allergic disorders, and inflammatory diseases as well as chronic infectious diseases involving viruses, bacteria, fungi or parasites, where effective treatment requires the quantity and quality of cellular immunity that combined NKT activator/CD40 agonist immunization is capable of generating.

Applications of the Invention

The invention provides novel adjuvant combinations comprising at least one NKT activator, at least one CD40 agonist and optionally an antigen. The invention embraces the use of any antigen in combination with the subject NKT activators and CD40 agonists against which an enhanced cellular immune response is therapeutically desirable. In some embodiments the antigen may be administered separate from the NKT activator, or the host may be naturally exposed to the antigen. In some embodiments all three moieties, i.e., the CD40 agonist such as anti-CD40 antibody, the NKT activator and the antigen, may be administered concurrently. Additionally, in some embodiments all three moieties, i.e., the CD40 agonist such as anti-CD40 antibody, the NKT activator and the antigen, may be co-administered as separate discrete entities. Preferably all these moieties are administered substantially concurrently in order to achieve the desired synergistic enhancement in cellular immunity. These moieties may be administered in any order.

Exemplary antigens include but are not limited to bacterial, viral, parasitic, allergens, autoantigens and tumor associated antigens. Particularly, the antigen can include protein antigens, peptides, whole inactivated organisms, and the like.

Specific examples of antigens that can be used in the invention include antigens from hepatitis A, B, C or D, influenza virus, *Listeria, Clostridium botulinum*, tuberculosis, tularemia, Variola major (smallpox), viral hemorrhagic fevers, *Yersinia pestis* (plague), HIV, herpes, pappilloma virus, and other antigens associated with infectious agents. Other antigens include antigens associated with a tumor cell, antigens associated with autoimmune conditions, allergy and asthma. Administration of such an antigen in conjunction with the subject agonist combination flagellin and an anti-CD40 antibody can be used in a therapeutic or prophylactic vaccine for conferring immunity against such disease conditions.

In some embodiments the methods and compositions can be used to treat an individual at risk of having an infection or has an infection by including an antigen from the infectious agent. An infection refers to a disease or condition attributable to the presence in the host of a foreign organism or an agent which reproduce within the host. A subject at risk of having an infection is a subject that is predisposed to develop an infection. Such an individual can include for example a subject with a known or suspected exposure to an infectious organism or agent. A subject at risk of having an infection can also include a subject with a condition associated with impaired ability to mount an immune response to an infectious agent or organism, for example a subject with a congenital or acquired immunodeficiency, a subject undergoing radiation or chemotherapy, a subject with a burn injury, a subject with a traumatic injury, a subject undergoing surgery, or other invasive medical or dental procedure, or similarly immunocompromised individual.

Infections which may be treated or prevented with the vaccine compositions of this invention include bacterial, viral, fungal, and parasitic. Other less common types of infection also include are rickettsiae, mycoplasms, and agents causing scrapie, bovine spongiform encephalopathy (BSE), and prion diseases (for example kuru and Creutzfeldt-Jacob disease). Examples of bacteria, viruses, fungi, and parasites that infect humans are well know. An infection may be acute, subacute, chronic or latent and it may be localized or systemic. Furthermore, the infection can be predominantly intracellular or extracellular during at least one phase of the infectious organism's agent's life cycle in the host.

Bacteria infections against which the subject vaccines and methods may be used include both Gram negative and Gram positive bacteria. Examples of Gram positive bacteria include but are not limited to *Pasteurella* species, Staphylococci species, and Streptococci species. Examples of Gram negative bacteria include but are not limited to *Escherichia coli, Pseudomonas* species, and *Salmonella* species. Specific examples of infectious bacteria include but are not limited to *Heliobacter pyloris, Borrelia burgdorferi, Legionella pneumophilia, Mycobacteria* spp. (far example *M. tuberculosis, M. avium, M. intracellilare, M. kansaii, M. gordonae*), *Staphylococcus aureus, Neisseria gonorrhoeae, Neisseria meningitidis, Listeria monocytogeners, Streptococcus pyogenes,* (group A *Streptococcus*), *Streptococcus agalactiae*(Group B *Streptococcus*), *Streptococcus* (viridans group), *Streptococcus faccalis, streptococcus bovis, Streptococcus (aenorobic* spp.), *Streptococcus pneumoniae,* pathogenic *Campylobacter* spp., *Enterococcus* spp., *Haemophilus influenzae, Bacillus anthracis, Corynebacterium diptheriae, Corynebacterium* spp., *Erysipelothrix rhusiopathie, Clostridium perfringens, Clostridium tetani, Enterobacter aerogenes, Klebsiella pneumoniae, Pasteurella multocida, Bacteroides* spp., *Fusobacterium nucleatum, Streptobacillus moniliformis, Treponema pallidum, Treponema pertenue, Leptospira, Rickettsia*, and *Actinomyces israelii*.

Examples of viruses that cause infections in humans include but are not limited to Retroviridae (for example human deficiency viruses, such as HIV-1 (also referred to as HTLV-III), HIV-II, LAC or IDLV-III/LAV or HIV-III and other isolates such as HIV-LP), Picornaviridae (for example poliovirus, hepatitis A, enteroviruses, human Coxsackie viruses, rhinoviruses, echoviruses), Calciviridae (for example strains that cause gastroenteritis), Togaviridae (for example equine encephalitis viruses, rubella viruses), Flaviviridae (far example dengue viruses, encephalitis viruses, yellow fever viruses) Coronaviridae (for example coronaviruses), Rhabdoviridae (for example vesicular stomata viruses, rabies viruses), Filoviridae (for example Ebola viruses) Paramyxoviridae (for example parainfluenza viruses, mumps viruses, measles virus, respiratory syncytial virus), Orthomyxoviridae (for example influenza viruses), Bungaviridae (for example Hataan viruses, bunga viruses, phleoboviruses, and Nairo viruses), Arena viridae (hemorrhagic fever viruses), Reoviridae (for example reoviruses, orbiviruscs, rotaviruses), Bimaviridae, Hepadnaviridae (hepatitis B Parvoviridae (parvoviruses), Papovaviridae (papilloma viruses, polyoma viruses), Adenoviridae (adenoviruses), Herpeviridae (for example herpes simplex virus (HSV) I and II, varicella zoster virus, pox viruses) and Iridoviridae (for example African swine fever virus) and unclassified viruses (for example the etiologic agents of Spongiform encephalopathies, the agent of delta hepatitis, the agents of non-A, non-B hepatitis (class 1 enterally transmitted; class 2 parenterally transmitted such as Hepatitis C); Norwalk and related viruses and astroviruses.

Examples of fungi include *Aspergillus* spp., *Coccidoides immitis, Cryptococcus neoformans, Candida albicans* and other *Candida* spp., *Blastomyces dermatidis, Histoplasma capsulatum, Chlamydia trachomatis, Nocardia* spp., and *Pneumocytis carinii*.

Parasites include but are not limited to blood-borne and/or tissue parasites such as *Babesia microti, Babesi divergans, Entomoeba histolytica, Giarda lamblia, Leishmania tropica, Leishmania* spp., *Leishmania braziliensis, Leishmania donovdni, Plasmodium falciparum, Plasmodium malariae, Plasmodium ovale; Plasmodium vivax, Toxoplasma gondii, Trypanosoma gambiense* and *Trypanosoma rhodesiense* (African sleeping sickness), *Trypanosoma cruzi* (Chagus' disease) and *Toxoplasma gondii*, flat worms, and round worms.

As noted this invention further embraces the use of the subject conjugates in treating proliferative diseases such as cancers, and, in a preferred embodiment, in treating melanoma. Cancer is a condition of uncontrolled growth of cells which interferes with the normal functioning of bodily organs and systems. A subject that has a cancer is a subject having objectively measurable cancer cells present in the subject's body. A subject at risk of developing cancer is a subject predisposed to develop a cancer, for example based on family history, genetic predisposition, subject exposed to radiation or other cancer-causing agent. Cancers which migrate from their original location and seed vital organs can eventually lead to the death of the subject through the functional deterioration of the affected organ. Hematopoietic cancers, such as leukemia, are able to out-compete the normal hematopoietic compartments in a subject thereby leading to hematopoietic failure (in the form of anemia, thrombocytopenia and neutropenia), ultimately causing death.

A metastasis is a region of cancer cells, distinct from the primary tumor location, resulting from the dissemination of cancer cells from the primary tumor to other parts of the body. At the time of diagnosis of the primary tumor mass, the subject may be monitored for the presence of metastases. Metastases are often detected through the sole or combined use of magnetic resonance imaging (MRI), computed tomography (CT), scans, blood and platelet counts, liver function studies, chest-X-rays and bone scans in addition to the monitoring of specific symptoms.

The adjuvant combinations and compositions containing according to the invention can be used to treat a variety of cancers or subjects at risk of developing cancer, by the inclusion of a tumor-associated-antigen (TAA), or DNA encoding. This is an antigen expressed in a tumor cell. Examples of such cancers include breast, prostate, colon, blood cancers such as leukemia, chronic lymphocytic leukemia, and the like. The vaccination methods of the invention can be used to stimulate an immune response to treat a tumor by inhibiting or slowing the growth of the tumor or decreasing the size of the tumor. A tumor associated antigen can also be an antigen expressed predominantly by tumor cells but not exclusively.

Additional cancers include but are not limited to basal cell carcinoma, biliary tract cancer, bladder cancer, bone cancer, brain and central nervous system (CNS) cancer, cervical cancer, choriocarcinoma, colorectal cancers, connective tissue cancer, cancer of the digestive system, endometrial cancer, esophageal cancer, eye cancer, head and neck cancer, gastric cancer, intraepithelial neoplasm, kidney cancer, larynx dancer, liver cancer, lung cancer (small cell, large cell), lymphoma including Hodgkin's lymphoma and non-Hodgkin's lymphoma; neuroblastoma; oral cavity cancer (for example lip, tongue, mouth and pharynx); ovarian cancer; pancreatic cancer; retinoblastoma; rhabdomyosarcoma; rectal cancer; cancer of the respiratory system; sarcoma; skin cancer; stomach cancer; testicular cancer; thyroid cancer; uterine cancer; cancer of the urinary system; as well as other carcinomas and sarcomas.

The adjuvant combinations and compositions containing according to the invention can also be used to treat autoimmune diseases such as multiple sclerosis, rheumatoid arthritis, type 1 diabetes, psoriasis or other autoimmune disorders. Other autoimmune disease which potentially may be treated with the vaccines and immune adjuvants of the invention include Crohn's disease and other inflammatory bowel diseases such as ulcerative colitis, systemic lupus eythematosus (SLE), autoimmune encephalomyelitis, myasthenia gravis (MG), Hashimoto's thyroiditis, Goodpasture's syndrome, pemphigus, Graves disease, autoimmune hemolytic anemia, autoimmune thrombocytopenic purpura, scleroderma with anti-collagen antibodies, mixed connective tissue disease, polypyositis, pernicious anemia, idiopathic Addison's disease, autoimmune associated infertility, glomerulonephritis (for example crescentic glomerulonephritis, proliferative glomerulonephritis), bullous pemphigoid, Sjogren's syndrome, psoriatic arthritis, insulin resistance, autoimmune diabetes mellitus (type 1 diabetes mellitus; insulin dependent diabetes mellitus), autoimmune hepatitis, autoimmune hemophilia, autoimmune lymphoproliferative syndrome (ALPS), autoimmune hepatitis, autoimmune hemophilia, autoimmune lymphoproliferative syndrome, autoimmune uveoretinitis, and Guillain-Bare syndrome. Recently, arteriosclerosis and Alzheimer's disease have been recognized as autoimmune diseases. Thus, in this embodiment of the invention the antigen will be a self-antigen against which the host elicits an unwanted immune response that contributes to tissue destruction and the damage of normal tissues.

The adjuvant combinations and compositions containing according to the invention can also be used to treat asthma and allergic and inflammatory diseases. Asthma is a disorder of the respiratory system characterized by inflammation and narrowing of the airways and increased reactivity of the airways to inhaled agents. Asthma is frequently although not exclusively associated with atopic or allergic symptoms. Allergy is acquired hypersensitivity to a substance (allergen). Allergic conditions include eczema, allergic rhinitis, or coryza, hay fever, bronchial asthma, urticaria, and food allergies and other atopic conditions. An allergen is a substance that can induce an allergic or asthmatic response in a susceptible subject. There are numerous allergens including pollens, insect venoms, animal dander, dust, fungal spores, and drugs.

Examples of natural and plant allergens include proteins specific to the following genera: *Canine, Dermatophagoides, Felis, Ambrosia, Lotium, Cryptomeria, Alternaria, Alder, Alinus, Betula, Quercus, Olea, Artemisia, Plantago, Parictaria, Blatella, Apis, Cupressus, Juniperus, Thuya, Chamaecyparis, Periplanet, Agopyron, Secale, Triticum, Dactylis, Festuca, Poa, Avena, Holeus, Anthoxanthum, Arrhenatherum, Agrostis, Phleum, Phalaris, Paspalum, Sorghum*, and *Bromis*.

It is understood that the adjuvant combinations and compositions containing according to the invention can be combined with other therapies for treating the specific condition, e.g., infectious disease, cancer or autoimmune condition. For example in the case of cancer the inventive methods may be combined with chemotherapy or radiotherapy.

Methods of making compositions as vaccines are well known to those skilled in the art. The effective amounts of the NKT activator, CD40 agonist and optionally an antigen can be determined empirically, but can be based on immunologically effective amounts in animal models. Factors to be considered include the antigenicity, the formulation, the route of administration, the number of immunizing doses to be administered, the physical condition, weight, and age of the individual, and the like. Such factors are well known to those skilled in the art and can be determined by those skilled in the art (see for example Paoletti and McInnes, eds., Vaccines, from Concept to Clinic: A Guide to the Development and Clinical Testing of Vaccines for Human Use CRC Press (1999)). As disclosed herein it is understood that the subject DNAs or protein conjugates can be administered alone or in conjunction with other adjuvants.

The adjuvants of the invention can be administered locally or systemically by any method known in the art including but not limited to intramuscular, intravenous, intradermal, subcutaneous, intraperitoneal, intranasal, oral or other mucosal routes. Additional routes include intracranial (for example intracisternal, or intraventricular), intraorbital, ophthalmic, intracapsular, intraspinal, and topical administration. The adjuvants and vaccine compositions of the invention can be administered in a suitable, nontoxic pharmaceutical carrier, or can be formulated in microcapsules or a sustained release implant. The immunogenic compositions of the invention can be administered multiple times, if desired, in order to sustain the desired cellular immune response. The appropriate route, formulation, and immunization schedule can be determined by one skilled in the art.

In the methods of the invention, in some instances the antigen and a NKT activator/CD40 agonist conjugate may be administered separately or combined in the same formulation. In some instances it may be useful to include several antigens. These compositions may be administered separately or in combination in any order that achieve the desired synergistic enhancement of cellular immunity. Typically, these compositions are administered within a short time of one another, i.e. within about several hours of one another, more preferably within about a half hour. In some embodiments they may be co-administered within about 24-48 hours of one another.

In some instances, it may be beneficial to include a moiety in the adjuvant which facilitates affinity purification. Such moieties include relatively small molecules that do not interfere with the function of the adjuvant combination. Alternatively, the tags may be removable by cleavage. Examples of such tags include poly-histidine tags, hemagglutinin tags, maltase binding protein, lectins, glutathione-S transferase, avidin and the like. Other suitable affinity tags include FLAG, green fluorescent protein (GFP), myc, and the like.

The subject adjuvant combinations can be administered with a physiologically acceptable carrier such as physiological saline. The composition may also include another carrier or excipient such as buffers, such as citrate, phosphate, acetate, and bicarbonate, amino acids, urea, alcohols, ascorbic acid, phospholipids, proteins such as serum albumin, ethylenediamine tetraacetic acid, sodium chloride or other salts, liposomes, mannitol, sorbitol, glycerol and the like. The adjuvants of the invention can be formulated in various ways, according to the corresponding route of administration. For example, liquid formulations can be made for ingestion or injection, gels or procedures can be made for ingestion, inhalation, or topical application. Methods for making such formulations are well known and can be found in for example, "Remington's Pharmaceutical Sciences," $18^{th}$ Ed., Mack Publishing Company, Easton Pa.

The invention also embraces DNA based vaccines. These DNAs which may encode a desired antigen and/or CD40 adjuvant may be administered as naked DNAs, or may be comprised in an expression vector. Furthermore, the subject nucleic acid sequences may be introduced into a cell of a graft prior to transplantation of the graft. This DNA preferably will be humanized to facilitate expression in a human subject.

The subject adjuvant combinations may further include a "marker" or "reporter." Examples of marker or reporter molecules include beta lactamase, chloramphenicol acetyltransferase, adenosine deaminase, aminoglycoside phosphotransferase, dihydrofolate reductase, hygromycin B-phosphotransferase, thymidine kinase, lacZ, and xanthine guanine phosphoribosyltransferase et al.

Prokaryotic and eukaryotic cells that can be used to facilitate expression of the subject adjuvants or antigens include by way of example microbia, plant and animal cells, e.g., prokaryotes such as *Escherichia coli, Bacillus subtilis*, and the like, insect cells such as Sf21 cells, yeast cells such as *Saccharomyces, Candida, Kluyveromyces, Schizzosaccharomyces*, and *Pichia*, and mammalian cells such as COS, HEK293, CHO, BHK, NIH 3T3, HeLa, and the like. One skilled in the art can readily select appropriate components for a particular expression system, including expression vector, promoters, selectable markers, and the like suitable for a desired cell or organism. The selection and use of various expression systems can be found for example in Ausubel et al., "Current Protocols in Molecular Biology, John Wiley and Sons, New York, N.Y. (1993); and Pouwels et al., Cloning Vectors: A Laboratory Manual"; 1985 Suppl. (1987). Also provided are eukaryotic cells that contain and express the subject DNA constructs.

In the case of cell transplants, the cells can be administered either by an implantation procedure or with a catheter-mediated injection procedure through the blood vessel wall. In some cases, the cells may be administered by release into the vasculature, from which the cells subsequently are distributed by the blood stream and/or migrate into the surrounding tissue.

The "NKT activators or agonists" useful in the invention include all activators or agonists of NKT cells generally known in the art. Examples of NKT activators r agonists include for example the ceramide and other glycolipid compounds disclosed inn US20060211856 and US20060052316, both of which published patent applications are incorporated by reference in their entirety herein. For example this includes alpha-galactosyl ceramide, alpha-glucosyl ceramide, phosphatidylinisitol and glycosylphosphatidylinisitol and the various other glycolipid compounds and derivatives disclosed in the cited patents as NKT activators and known in the art. See also Parekh et al., Crit. Rev. Immunol. 25)3):183-213 (2005); and Parekh et al., J Immunol. 173(1):3693-706 (2006), both of which references are also incorporated by reference in their entirety herein.

The "CD40 agonists" useful in the invention as noted preferably comprise an agonistic anti-CD40 antibody or fragment thereof that specifically binds CD40, preferably murine or human CD40 or a CD40L protein, derivative, multimer such as a trimeric CD40L conjugate. As used herein, the term "antibody" is used in its broadest sense to include polyclonal and monoclonal antibodies, as well as antigen binding fragments thereof. This includes Fab, F(ab') 2, Fd and Fv fragments.

In addition the term "antibody" includes naturally antibodies as well as non-naturally occurring antibodies such as single chain antibodies, chimeric antibodies, bifunctional and humanized antibodies. Preferred for use in the invention are chimeric, humanized and fully human antibodies. Methods for synthesis of chimeric, humanized, CDR-grafted, single chain and bifunctional antibodies are well known to those skilled in the art. In addition, antibodies specific to CD40 are widely known and available and can be made by immunization of a suitable host with a CD40 antigen, preferably human CD40.

It is understood that modifications which do not substantially affect the activity of the various embodiments of this invention are also provided within the definition of the invention provided herein.

EXAMPLES

Synergy of CD40 agonists with α-GalCer in inducing antigen-specific CD8 responses.

The following experiments reveal that that a NKT alpha-galactosylceramide (α-GalCer) synergizes with anti-CD40 antibodies in expanding CD8 cells with lytic function, similar to what has been previously observed with TLR agonists. Combined administration of a CD40 agonist and α-GalCer induced high levels of cell-mediated immunity.

Example 1

Combined administration of Anti-CD40 and α-GalCer synergistically enhances the expansion of antigen-specific T cells in vivo.

Figure 1:
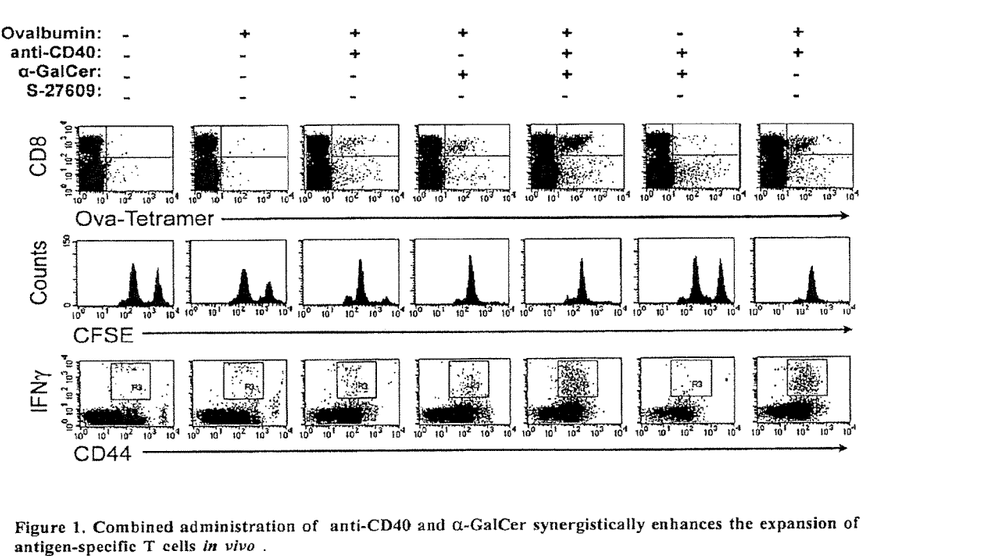
FIG. 1 contains an experiment showing the effect of combined administration of anti-CD40 and α-GalCer and that such administration synergistically enhances the expansion of antigen-specific T cells in vivo.

This example relates to the experiment contained in FIG. 1. Therein mice were administered 500 ug Ovalbumin, 100 ug anti-CD40, 100 ug S-27609 (TLR7 agonist), 4 ug α-Gal-Cer, i.v. in the combinations noted in the figure. Five days later, standard CTL assay with Siinfekl pulsed targets was performed, as previously described. On day six after administration of the reagents noted, the number of OVA-specific, $CD8^+$ T cells was determined by tetramer staining, as previously described as well as the number of antigen-specific $CD8^+$ T cells producing IFNγ after restimulation in vitro.

The results in FIG. 1 surprisingly demonstrate that the administration of a neoantigen (OVA) in combination with a CD40 agonist (anati-CD40) and a TLR agonist (S-27609) or anti-CD40 with α-GalCer induces high levels of OVA-specific, $CD8^+$ T cells (determined by tetramer staining using a OVA-H-2b tetramer) and recall responses of OVA-specific $CD8^+$ T cells to produce IFN-α.

Example 2

Quantifying immune responses as a result of immunization with combined anti-CD40 and α-GalCer (Based on Data in FIG. 1) and Demonstration of Synergy of CD40 agonists with α-GalCer in inducing protective anti-tumor immunity.

Because the administration of anti-CD40/α-GalCer/OVA or anti-CD40/609/OVA as compared to the use of the agents alone as monotherapies is far more effective at enhancing the total number of antigen-specific $CD8^+T$ cells, combination therapy was tested as an effective means to induce therapeutic immunity in a murine model of melanoma. Initial studies using anti-CD40 and TLR* or α-GalCer demonstrated that the administration of this combination of activators together with peptide or whole protein elicited extremely high (>5% tetramer$^+$T cells of the $CD8^+T$ cells) frequencies of antigen-specific cytotoxic T cells. We then wanted to explore whether high frequencies of "self-reactive or tumor-reactive" T cells could be elicited to protect against a syngeneic tumor. Tyrosinase-related protein-2 (TRP-2) is a protein involved in melanin synthesis and has been used as a melanoma-associated antigen for immunotherapy. TRP-2 is expressed in normal melanocytes and melanomas and has been identified as a human tumor antigen recognized by CTLs and subsequently identified as a tumor rejection antigen for B16 melanoma. $CD8^+T$ cell peptide epitopes have been described both for human and mouse. To test if anti-self-reactive $CD8^+T$ cells could be induced using the CD40/TLR platform, mice which were given B16 melanoma (four days prior) were immunized i.p with 50 ug of a heterocyclic version of TRP-2 (ΔV peptide; TRP-2 (SVYD-FFVWL (SEQ ID NO. 1)), anti-CD40 and TLR7* or anti-CD40 and α-GalCer (and monotherapies of each).

Figure 2:
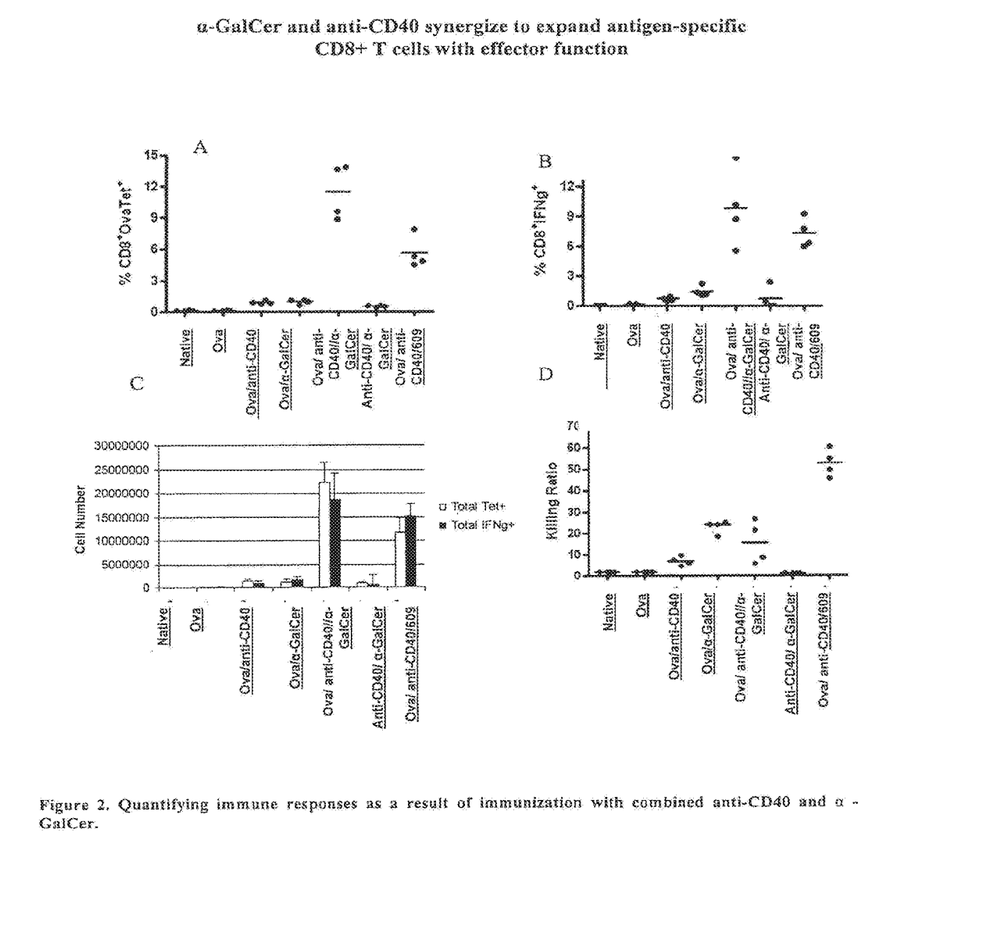
FIG. 2 contains an experiment that quantifies immune responses as a result of immunization with combined anti-CD40 and α-GalCer.

The results in FIG. 2 show that the most effective therapeutic protection was afforded by the combined use of anti-CD40/TLR/ΔV or anti-CD40/α-GalCer/ΔV, as judged by the number of lung metastases 21 days after administration of the tumor. Some prophylactic protection is afforded by α-GalCer and ΔV. However, based on our experience with other therapies, the use of anti-CD40/α-GalCer/ΔV will result in enhanced survival of those mice, as compared to mice receiving α-GalCer/ΔV therapy.

The in vivo killing assay also suggests that combination therapy (OVA/anti-CD40/α-GalCer) is also more effective then any monotherapy (anti-CD40/OVA or α-GalCer/OVA or TLR/OVA) tested (see FIG. 2).

Example 3

CD40/TLR* vaccination therapeutically intervenes in systemic melanoma.

Figure 3:
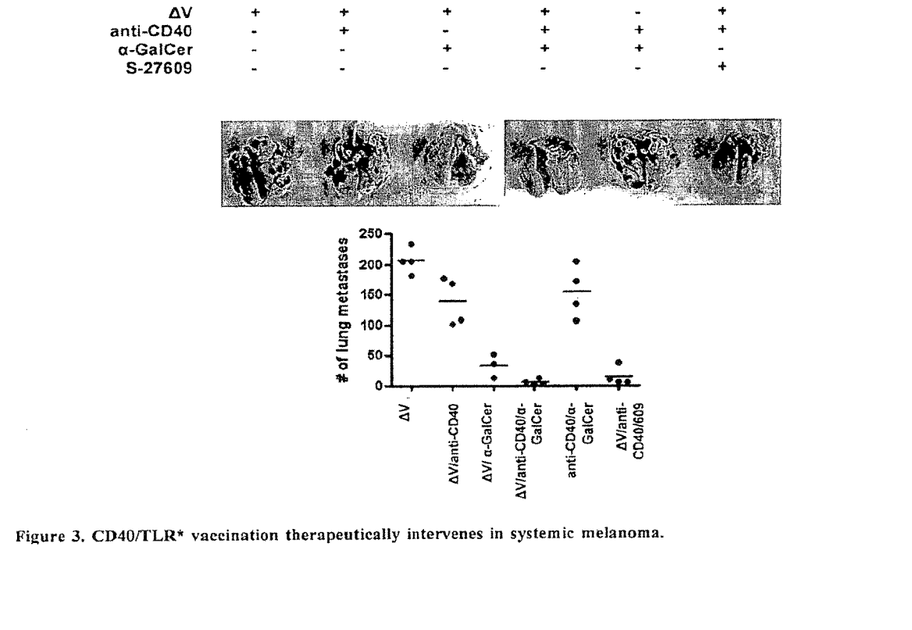
FIG. 3 contains an experiment in mice immunized with melanoma cells showing that CD40/TLR* vaccination therapeutically intervenes in systemic melanoma.

This example relates to the experiment contained in FIG. 3. In this experiment contained in FIG. 3, B6 mice (4/group) were immunized four days after the i.v. injection of 100K B16-F10 tumor cells. Particularly, mice were immunized with the combination of agents noted: Anti-CD40 (100 ug/mouse, i.p.), S27609 (TLR*) 100 ug), ΔV-peptide (100 ug), or α-GalCer (4 ug), i.v. Twenty days after administration of tumor (using a Day+4 intervention scheme) lungs were removed (see representative photo; top in FIG. 3) and the number of lung metastases quantified by visual counting (see bottom panel of FIG. 3).

Example 4

Anti-CD40 antibody and α-GalCer induces CD70 expression on DCs in vivo.

Figure 4:
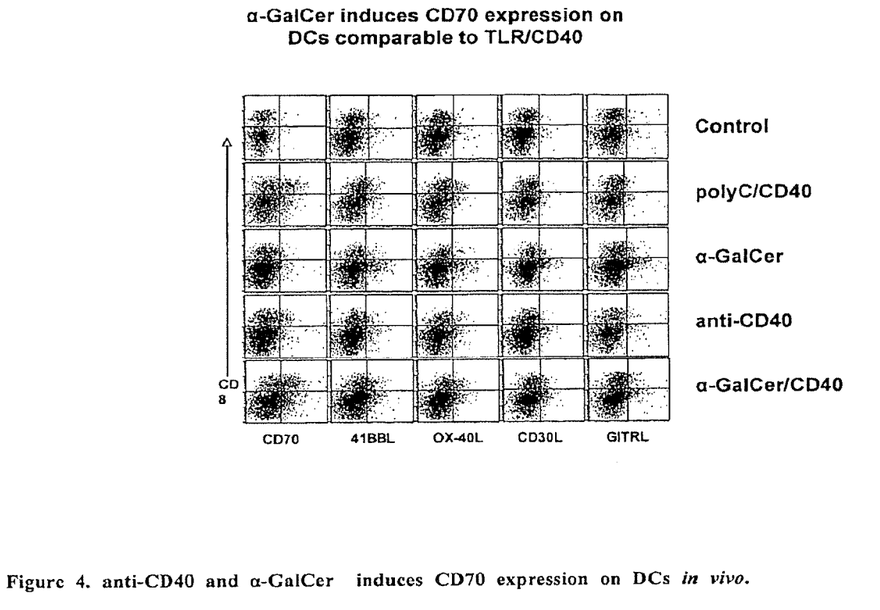
FIG. 4 contains an experiment showing that anti-CD40 and α-GalCer administration induces CD70 expression on DCs in vivo. (In this experiment mice were injected with combinations of the following: 2 ug α-GalCer, 50 ug polyIC, and/or 50 ug anti-CD40 i.p. Spleens were taken at 18-20 hours post injection).

In the experiment contained in FIG. 4, mice were injected with combinations of the following: 2 ug α-GalCer, 50 ug polyIC, and/or 50 ug anti-CD40 i.p. Afterward, spleens were taken at 18-20 hours post injection. The spleens were collagenase digested, stained for CD11c+ and analyzed by CD8+ and CD8− (CD11b+) DCs.

The results in this Figure unexpectedly reveal that the expression of CD70 is only induced on dendritic cells obtained from mice which were administered the combination of a CD40 agonist and α-GalCer.

The present inventors have previously reported that only when both anti-CD40 and TLR agonists are administered in combination that there is an increase in CD70 expression on the surface of dendritic cells in vivo. In addition, we have shown that expression of CD70 is essential for the subsequent expansion of antigen-specific CD8$^+$ T cells.

Quite unexpectedly, similar results are observed with the administration of the subject novel synergistic adjuvant combinations. Particularly, and similar to the synergy seen with TLR and CD40 agonists, upregulation of CD70 on DCs is also seen by the combined administration anti-CD40 and α-GalCer. As shown in FIG. 4, there is observed significantly increased expression of CD70 on CD8$^+$ and CD8−, CD11c$^+$ DCs only when anti-CD40 and TLR agonist (polyIC) or when anti-CD40 and α-GalCer are administered.

Example 5

α-GalCer/CD40 immunization elicits a potent CD8+ T cell response that is STAT4, IFNγ and IFNab independent but is STAT1 and Tbet dependent.

The Signal Transducers and Activator of Transcription (STAT) proteins regulate many aspects of cell growth. STAT1 is involved in upregulating genes due to a signal by either type I or type II interferons. In response to TIN-γ stimulation, STAT1 forms homodimers or heterodimers with STAT3 that bind to the GAS (Interferon-Gamma Activated Sequence) promoter element; in response to either IFN-α or IFN-β stimulation, STAT1 forms a heterodimer with STAT2 that can bind the ISRE (Interferon Stimulated Response Element) promoter element. The role of IL-12 in cellular immunity is largely mediated by the STAT-4 transcription factor. STAT-4 is essential for IL-12 activity. T-bet is a member of the T-box family of transcription factors that regulates lineage commitment in CD4 (TH) lymphocytes. This is done part by activating IFN-γ. T-bet is required for control of IFN- production in CD4 and NK cells, but not in CD8 cells.

Figure 5:
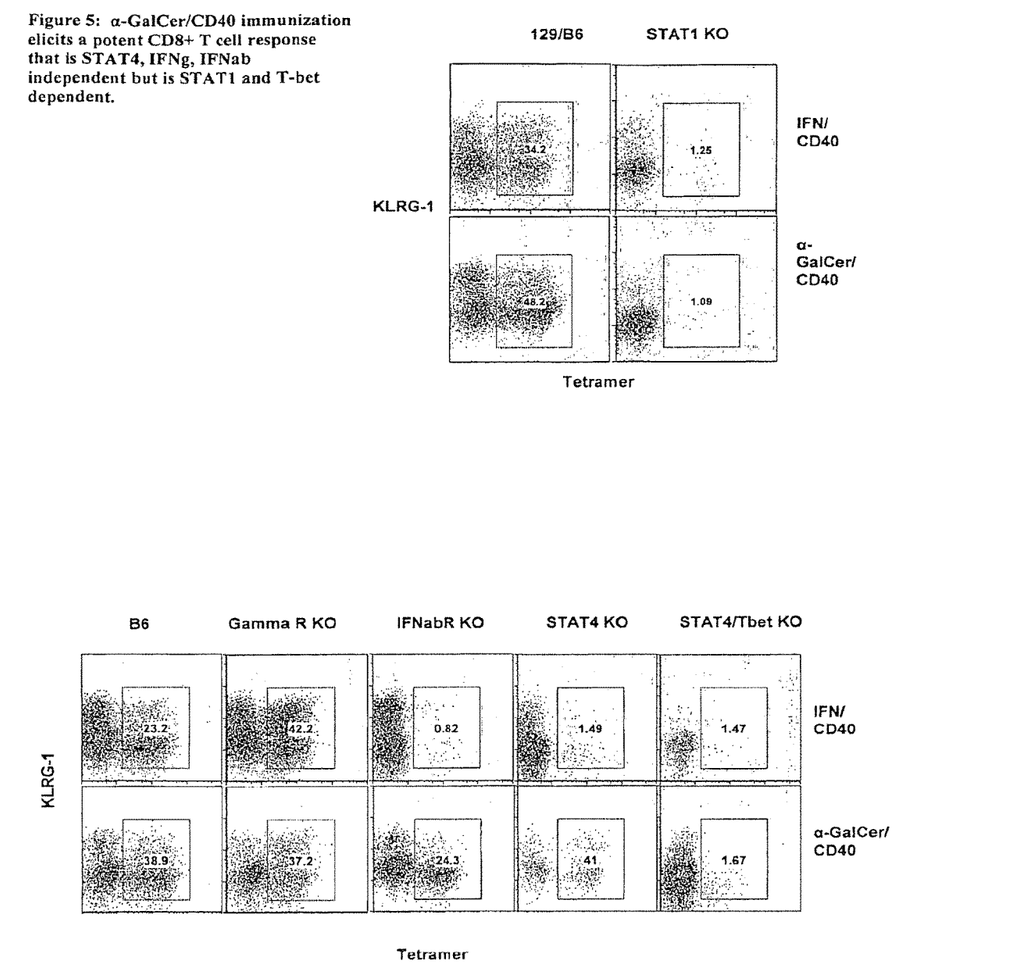
FIG. 5 contains an experiment showing that α-GalCer/CD40 immunization elicits a potent CD8+ T cell response that is STAT4, IFNγ and IFNab independent but is STAT1 and T-bet independent.

In the experiment contained in FIG. 5, mice (wtB6 or wtB6/129F1's and KO) were immunized I.V. with 50 ug ant-CD40 (FGK45), 2 ug α-GalCer, and 200 ug of whole ovalbumin. Seven days later, the mice were sacrificed and PBLs and spleen cells isolated and stained with Kb/ova MHC tetramers to identify ova-specific CD8+ T cells as previously described (Sanchez et al. 2007 Journal of Immunology). The dot plots shown are gated on all live, CD8+ B220− cells and the phenotype of the tetramer + and − cells is shown with respect to the surface marker KLRG1. Numbers shown represent the percent tetramer+ out of total CD8+ T cells. Dot plots shown are for PBL, but spleen reflects similar trends. This experiment indicates that α-Gal-Cer/CD40 immunization elicits a potent CD8+ T cell response that is STAT4, IFNγ and IFNab independent but is STAT1 and T-bet independent.

CONCLUSIONS

Based at least on the results contained in the experiments in FIGS. 1-5, the combined administration of a CD40 agonist, together with antigen and an agonist that triggers NK-T cells (α-GalCer) induces immunity that is heightened over any of these agonists alone (elicits a synergistic effect on immunity). The combination of CD40 agonist and α-GalCer results in higher frequencies of antigen-specific CD8$^+$ T cells, higher numbers of antigen-specific CD8$^+$ T cells and enhance anti-tumor immunity when compared to any agonist alone with or without antigen.

Therefore, the combined use of a CD40 agonist and a NK-T cell activator, like α-GalCer, will serve as a potent vaccine platform in eliciting protective cell-mediated immune responses to tumors and infectious disease.

The various references to journals, patents, and other publications which are cited herein comprise the state of the art and are incorporated by reference as though fully set forth.

The invention is further defined by the claims which follow.

---

---

The invention claimed is:

1. An adjuvant combination consisting essentially of:
   (i) at least one agonist of CD40 comprising an agonistic anti-CD40 antibody or antibody fragment or an agonistic CD40L polypeptide, wherein said agonistic anti-CD40 antibody is a monoclonal antibody selected from CD40.4 (5c3) and S2C6;

(ii) at least one NKT activator comprising alpha-galactosylceramide (alpha-Gal-Cer) or iGb3; and
(iii) at least one infectious agent antigen;
wherein the administration of said adjuvant combination elicits a synergistic enhancement of CD70 expression on an immune cell relative to either the agonist of CD40 or the alpha-Gal-Cer administered as a monotherapy.

2. The adjuvant combination of claim 1, wherein the infectious agent is a virus.

3. The adjuvant combination of claim 1, wherein the infectious agent is a parasite.

4. The adjuvant combination of claim 1, wherein the infectious agent is a bacterium or a fungus.

5. The adjuvant combination of claim 1, wherein the antigen is a viral antigen from a virus selected from the group consisting of HIV, herpes, papillomavirus, Ebola, picorna virus, enterovirus, measles virus, mumps virus, bird flu virus, rabies virus, VSV, dengue virus, hepatitis virus, rhinovirus, yellow fever virus, bunga virus, polyoma virus, coronavirus, rubella virus, echovirus, pox virus, varicella zoster, African swine fever virus, influenza virus and parainfluenza virus.

6. The adjuvant combination of claim 1, wherein the antigen is a bacterial antigen of a bacterium selected from the group consisting of *Salmonella, Escherichia, Pseudomonas, Bacillus, Vibrio, Campylobacter, Helicobacter, Erwinia, Borrelia, Pelobacter, Clostridium, Serratia, Xanthomonas, Yersinia, Burkholderia, Listeria, Shigella, Pasteurella, Enterobacter, Corynebacterium* and *Streptococcus*.

7. The adjuvant combination of claim 1, wherein the antigen is a parasite antigen of a parasite selected from *Babesia, Entamoeba, Leishmania, Plasmodium, Trypanosoma, Toxoplasma, Giardia*, flat worms and round worms.

8. The adjuvant combination of claim 1, wherein the antigen is a fungal antigen from a fungus selected from the group consisting of *Aspergillus, Coccidioides, Cryptococcus, Candida Nocardia, Pneumocystis*, and *Chlamydia*.

9. The adjuvant combination of claim 1, wherein the CD40 agonist is an agonistic CD40 antibody or antibody fragment.

10. The adjuvant combination of claim 2, wherein the CD40 agonist is an agonistic CD40 antibody or antibody.

11. The adjuvant combination of claim 1, wherein the CD40 agonist is an anti-CD40 agonistic antibody or antibody fragment, and the antigen is a hepatitis antigen.

12. The adjuvant combination of claim 1, wherein the CD40 agonist is an anti-CD40 agonistic antibody or antibody fragment, and the antigen is a papillomavirus antigen.

13. The adjuvant combination of claim 1, wherein the CD40 agonist is an agonistic CD40L polypeptide.

* * * * *